US007799832B2

(12) United States Patent
Szelenyi et al.

(10) Patent No.: US 7,799,832 B2
(45) Date of Patent: *Sep. 21, 2010

(54) COMBINATIONS OF RETIGABINE AND SODIUM CHANNEL INHIBITORS OR SODIUM CHANNEL-INFLUENCING ACTIVE COMPOUNDS FOR TREATING PAINS

(75) Inventors: Istvan Szelenyi, Schwaig (DE); Kay Brune, Marloffstein (DE); Robert Hermann, Hanau (DE); Mathias Locher, Ronneburg (DE)

(73) Assignee: Valeant Pharmaceuticals North America, Aliso Viejo, CA (US)

( * ) Notice: Subject to any disclaimer, the term of this patent is extended or adjusted under 35 U.S.C. 154(b) by 450 days.

This patent is subject to a terminal disclaimer.

(21) Appl. No.: 10/727,655

(22) Filed: Dec. 5, 2003

(65) Prior Publication Data

US 2005/0090547 A1 Apr. 28, 2005

(30) Foreign Application Priority Data

Oct. 23, 2003 (DE) ................................ 103 49 729

(51) Int. Cl.
*A61K 31/44* (2006.01)
*A61K 31/24* (2006.01)
(52) U.S. Cl. ...................................... 514/537; 514/355
(58) Field of Classification Search ................. 514/485, 514/535, 352
See application file for complete search history.

(56) References Cited

U.S. PATENT DOCUMENTS

| 4,554,281 | A | | 11/1985 | vonBebenburg et al. |
| 4,668,684 | A | | 5/1987 | Tibes et al. |
| 4,778,799 | A | | 10/1988 | Tibes et al. |
| 4,923,858 | A | | 5/1990 | Engel et al. |
| 5,032,591 | A | | 7/1991 | Evans et al. |
| 5,234,947 | A | | 8/1993 | Cherksey |
| 5,262,419 | A | | 11/1993 | Aberg et al. |
| 5,384,330 | A | * | 1/1995 | Dieter et al. ................. 514/535 |
| 5,428,039 | A | | 6/1995 | Cohen |
| 5,502,058 | A | * | 3/1996 | Mayer et al. ................. 514/289 |
| 5,643,921 | A | | 7/1997 | Grover |
| 5,679,706 | A | | 10/1997 | D'Alonzo et al. |
| 5,760,007 | A | * | 6/1998 | Shank et al. ................... 514/23 |
| 5,800,385 | A | | 9/1998 | Demopulos et al. |
| 5,849,789 | A | * | 12/1998 | Rostock et al. ............. 514/485 |
| 5,852,053 | A | * | 12/1998 | Rostock et al. ............. 514/485 |
| 5,858,017 | A | | 1/1999 | Demopulos et al. |
| 5,860,950 | A | | 1/1999 | Demopulos et al. |
| 5,914,425 | A | | 6/1999 | Meisel et al. |
| 6,117,900 | A | * | 9/2000 | Rundfeldt et al. ........... 514/485 |
| 6,218,411 | B1 | | 4/2001 | Koga |
| 6,265,417 | B1 | | 7/2001 | Carroll |
| 6,281,211 | B1 | * | 8/2001 | Cai et al. ................. 514/237.5 |
| 6,326,385 | B1 | | 12/2001 | Wickenden et al. |
| 6,348,486 | B1 | * | 2/2002 | Argentieri et al. ............ 514/411 |
| 6,395,736 | B1 | | 5/2002 | Parks et al. |
| 6,469,042 | B1 | | 10/2002 | Hewawasam et al. |
| 6,472,165 | B1 | * | 10/2002 | Rundfeldt et al. .............. 435/29 |
| 6,495,550 | B2 | | 12/2002 | McNaughton-Smith et al. |
| 6,500,455 | B1 | * | 12/2002 | Frantsits ..................... 424/463 |
| 6,538,004 | B2 | | 3/2003 | Drizin |
| 6,538,151 | B1 | | 3/2003 | Meisel et al. |
| 6,589,986 | B2 | | 7/2003 | Bowlby et al. |
| 6,593,335 | B1 | | 7/2003 | Carroll |
| 6,642,209 | B1 | * | 11/2003 | Fukunaga ..................... 514/46 |
| 6,645,521 | B2 | * | 11/2003 | Cassel ........................ 424/449 |
| 6,737,422 | B2 | | 5/2004 | McNaughton-Smith et al. |
| 7,045,551 | B2 | | 5/2006 | Wu et al. |
| 7,160,684 | B2 | | 1/2007 | Argentieri et al. |
| 7,309,713 | B2 | | 12/2007 | Rundfeldt et al. |
| 2002/0013349 | A1 | | 1/2002 | Wickenden |
| 2002/0015730 | A1 | | 2/2002 | Hoffmann et al. |
| 2002/0183395 | A1 | | 12/2002 | Argentieri |
| 2004/0198724 | A1 | | 10/2004 | McNaughton-Smith et al. |
| 2005/0089473 | A1 | | 4/2005 | Black et al. |
| 2005/0089559 | A1 | | 4/2005 | Szelenyi |
| 2005/0090547 | A1 | | 4/2005 | Szelenyi |
| 2005/0202394 | A1 | | 9/2005 | Dobson |
| 2005/0277579 | A1 | | 12/2005 | Krishnan et al. |
| 2007/0066612 | A1 | | 3/2007 | Khanzhin et al. |

FOREIGN PATENT DOCUMENTS

| CA | 2542434 | | 5/2005 |
| DE | 3337593 | | 10/1983 |
| DE | 3604575 | A1 | 8/1986 |
| EP | 189788 | A1 | 8/1986 |

(Continued)

OTHER PUBLICATIONS

"A Comparative Evaluation of the Effects of propafenone and Lidocaine one Early Ventricular Arrhythmias after Acute Myocardial Infarction", Touboul et al., European Heart Journal, abstract, 1998, vol. 9, No. 11, pp. 1188-1193.*

(Continued)

*Primary Examiner*—Brian-Yong S Kwon
(74) *Attorney, Agent, or Firm*—McDermott Will & Emery LLP

(57) ABSTRACT

The invention relates to pharmaceutical combinations of retigabine and sodium channel inhibitors for treating pains which are accompanied by an increase in muscle tone.

11 Claims, No Drawings

FOREIGN PATENT DOCUMENTS

| | | |
|---|---|---|
| EP | 0 343 429 | 5/1989 |
| EP | 1 334 972 | 8/2003 |
| EP | 1407768 A2 * | 4/2004 |
| JP | 2000 143510 | 5/2000 |
| JP | 2000-143510 A | 5/2000 |
| JP | 2000 143510 A | 5/2000 |
| WO | WO 00/55137 | 9/2000 |
| WO | WO 00/59487 A2 | 10/2000 |
| WO | WO 00/59508 A1 | 10/2000 |
| WO | WO 01/01970 | 1/2001 |
| WO | WO 01/01970 A2 | 1/2001 |
| WO | WO 01/09612 | 2/2001 |
| WO | WO 01/22953 A2 | 4/2001 |
| WO | WO 02/080898 | 10/2002 |
| WO | WO 03/020706 | 3/2003 |
| WO | WO 03/097586 | 11/2003 |
| WO | WO 2004/058739 | 7/2004 |
| WO | WO 2004/080950 | 9/2004 |
| WO | WO 2004/082677 | 9/2004 |
| WO | WO 2004/096767 | 11/2004 |
| WO | WO 2004/105795 | 12/2004 |
| WO | WO 2005/048975 | 6/2005 |
| WO | WO 2005/087754 | 9/2005 |
| WO | WO 2005/100349 | 10/2005 |
| WO | WO 2006/029623 | 3/2006 |
| WO | WO 2006/092143 | 9/2006 |
| WO | WO 2008/024398 | 2/2008 |
| WO | WO 2008/066900 | 6/2008 |

OTHER PUBLICATIONS

"Sodium channels are Required during in Vivo Sodium chloride Hyperosmolarity to Stimulate Increase in Intestinal Endothelial Nitric Oxide Production", Zani et al., Am J Physiolo Heart Cir. Physiol 288: H89-H95, 2005.*
Kuo et al., Inhibition of Na+ Current by Diphenhydramine and Other Diphenyl Compounds . . . , Molecular Pharmacology, 2000, 57(1):135-143.
Beck et al., Kreuzschmerzen in der Gynaekologischen Praxis, Gynaekologe, Springer Verlag, Berlin Germany, 2002, 35(5):490-494.
Armand et al., "Effects of retigabine (D-23129) on different patterns of epileptiform activity induced by 4-aminopyridine in rat entorhinal cortex hippocampal slices," *Naunyn-Schmiedeberg's Arch Pharmacol* 359:33-39 (1999).
Armijo et al., "Ion channels and epilepsy," *Curr Pharm Des.* 11:1975-2003 (2005).
Barhanin, M., et al., "$K_v$LQT1 and ISK (minK) proteins associate to form the $I_{Ks}$ cardiac potassium current," *Nature* 384(6604):78-80 (1996).
Beeby et al. "The synthesis and properties of 2:7-Disubstituted 1:2:3:4-tetrahydroisoquinolines," *J. Chem. Soc.* ¶ 385, 1799-1803 (1949).
Bialer et al., "Progress report on new antiepileptic drugs: a summary of the fourth Eilat conference (EILAT IV)," *Epilepsy Res.* 34:1-41 (1999).
Bialer, "Progress report on new antiepileptic drugs: a summary of the Sixth Eilat Conference (EILAT VI)," *Epilepsy Res.* 51:31-71 (2002).
Bialer, "Progress report on new antiepileptic drugs: a summary of the Seventh Eilat Conference (EILAT VII)," *Epilepsy Res.* 61:1-48 (2004).
Biervert et al., "A potassium channel mutation in neonatal human epilepsy," *Science* 279:403-406 (1998).
Blackburn-Munro and Jensen, "The anticonvulsant retigabine attenuates nociceptive behaviours in rat models of persistent and neuropathic pain," *Eur J. Pharmacol.* 460: 109-116 (2003).
Brown and Adams, "Muscarinic suppression of a novel voltage-sensitive K+ current in a vertebrate neurone," *Nature* 283:673-676 (1980).
Brown, D.A., *Ion Channels*, T. Narahashi, Ed. (Plenum Press, New York) pp. 55-94 (1988).

Charlier et al., "A pore mutation in a novel KQT-like potassium channel gene in an idiopathic epilepsy family," *Nat Genet.* 18:53-55 (1998).
Cooper et al., "Colocalization and coassembly of two human brain M-type potassium channel subunits that are mutated in epilepsy." *Proc Natl Acad Sci USA* 97:4914-4919 (2000).
Delmas and Brown, "Pathways modulating neural KCNQ/M (Kv7) potassium channels," *Nat Rev Neurosci.* 6:850-862 (2005).
Dickenson al., "Neurobiology of neuropathic pain: mode of action of anticonvulsants," *Eur. J. Pain* 6:51-60 (2002).
Dost et al., "The anticonvulsant retigabine potently suppresses epileptiform discharges in the low Ca ++ and low Mg++ model in the hippocampal slice preparation," *Epilepsy Res.* 38:53-56 (2000).
Friedel and Fitton, "Flupirtine: a review of its analgesic properties, and therapeutic efficacy in pain states," *Drugs* 45:548-569 (1993).
Hiller et al., "Retigabine N-glucuronidation and its potential role in enterohepatic circulation," *Drug Metab Dispos.* 27(5):605-612 (1999).
Hunt and Mantyh, "The molecular dynamics of pain control," *Nat Rev Neurosci.* 2:83-91 (2001).
Jentsch, "Neuronal KCNQ potassium channels; physiology and role in disease," *Nat. Rev Neurosci.*, 1:21-30 (2000).
Jiang et al., "X-ray structure of a voltage-dependent K+ channel," *Nature* 423:33-41 (2003).
Kharkovets et al., "Mice with altered KCNQ4 K+ channels implicate sensory outer hair cells in human progressive deafness," *EMBO J* 25:642-652 (2006).
Kibbe *Handbook of Pharmaceutical Excipients* (Pharmaceutical Press, London) (2000).
Kubisch et al., "KCNQ4, a novel potassium channel expressed in sensory outer hair cells, is mutated in dominant deafness," *Cell* 96:437-446 (1999).
Lamas et al., "Effects of a cognition-enhancer, linopirdine (DuP 996), on M-type potassium currents ($I_{K(M)}$) and some other voltage- and ligand-gated membrane currents in rat sympathetic neurons," *Eur. J Neurosci.*, 9:605-616 (1997).
Lee et al., "Structure of the KvAP voltage-dependent K+ channel and its dependence on the lipid membrane," *Proc Natl Acad Sci USA* 102:15441-15446 (2005).
Long et al., "Crystal Structure of a mammalian voltage-dependent *Shaker* family K+ channel," *Science* 309:897-903 (2005).
Main et al., "Modulation of KCNQ2/3 potassium channels by the novel anticonvulsant retigabine," *Mol. Pharmacol.* 58:253-262 (2000).
Marrion, "Control of M-currents," *Annu Rev Physiol.* 59:483-504 (1997).
Parcej and Eckhardt-Strelau, Structural characterization of neuronal voltage-sensitive K+ channels heterologously expressed in *Pichia pastoris*, *J Mol Biol* 333:103-116 (2003).
Passmore et al., "KCNQ/M currents in sensory neurons: significance for pain therapy," *J. Neurosci.* 23:7227-7236 (2003).
Porter et al., "Retigabine," *Neurotherapeutics* 4:149-154 (2007).
Reich et al., "Design and synthesis of novel 6,7-imidazotetrahydroquinoline inhibitors of thymidylate synthase using iterative protein crystal structure analysis," *J. Med. Chem.* 35:847-858 (1992).
Rogawski, Ma, "KCNQ2/KCNQ3 K+ channels and the molecular pathogenesis of epilepsy: implications for therapy," *Trends Neurosci.* 23:393-398 (2000).
Rostock et al., "A new anticonvulsant with broad spectrum activity in animal models of epileptic seizures," *Epilepsy Res.*23:211-223 (1996).
Rundfeldt et al., "Multiple actions of the new anticonvulsant D-23129 on voltage-gated inward currents and GABA-induced currents in cultured neuronal cells (abstract)," *Naunyn-Schmiedeberg's Arch Pharmacol* 351 (Suppl):R160 (1995).
Rundfeldt, "Characterization of the K+ channel opening effect of the anti-convulsant retigabine in PC12 cells," *Epilepsy Res.*35:99-107 (1999).
Rundfeldt, "The new anticonvulsant retigabine (D23129) acts as an opener of K+ channels in neuronal cells," *Eur J Pharmacol.* 336:243-249 (1997).

Schroeder et al., "KCNQ5, a novel potassium channel broadly expressed in brain, mediates M-type currents," *J. Biol. Chem.* 275:24089-24095 (2000).

Schroeder, "Moderate loss of function of cyclic-AMP-modulated KNCQ2/KCNQ3 $K^+$ channels causes epilepsy," *Nature* 396:687-690 (1998).

Singh et al., "A novel potassium channel gene, KCNQ2, is mutated in an inherited epilepsy of newborns," *Nat Genet.* 18:25-29 (1998).

Suzuki and Dickenson, "Neuropathic pain: nerves bursting with excitement," *NeuroReport* 11:R17-R21 (2000).

Tatulian and Brown, "Effect of the KCNQ potassium channel opener retigabine on single KCNQ2/3 channels express in CHO cells," *J Physiol.* 549:57-63 (2003).

Tatulian et al., "Activation of expressed KCNQ potassium currents and native neuronal M-type potassium currents by the anti-convulsant drug retigabine," *J. Neurosci.* 21:5535-5545 (2001).

Tober et al., "D-23129: a potent anticonvulsant in the amygdala kindling model of complex partial seizures," *Eur J Pharmacol*, 303:163-169 (1996).

Von Bebenburg et al., "Substituierte Polyaminopyridine" *Chemiker-Zeitung* 103:387-399 (1979). (German language article attached).

Wang et al., KCNQ2 and KCNQ3 potassium channel subunits: molecular correlates of the M-channel, *Science* 282:1890-1893 (1998).

Wang et al., "Positional cloning of a novel potassium channel gene: KVLQT1 mutations cause cardiac arrhythmias," *Nat Genet* 12:17-23 (1996).

Watanbe et al., "Disruption of the epilepsy KCNQ2 gene results in neural hyperexcitability," *J. Neurochem* 75:28-33 (2000).

Wickenden et al., "KCNQ potassium channels: drug targets for the treatment of epilepsy and pain," *Exp. Opin Thera Patents* 14(4): 457-469 (2004).

Wickenden et al., "Retigabine, a novel anti-convulsant, enhances activation of KCNQ2/Q3 potassium channels," *Mol. Pharmacol.* 58:591-600 (2000).

Wuttke, "The new anticonvulsant retigabine favors voltage-dependent opening of the Kv7.2 (KCNQ2) channel by binding to its activation gate," *Mol. Pharmacol.* 67:1009-1017 (2005).

\* cited by examiner

COMBINATIONS OF RETIGABINE AND SODIUM CHANNEL INHIBITORS OR SODIUM CHANNEL-INFLUENCING ACTIVE COMPOUNDS FOR TREATING PAINS

The invention relates to pharmaceutical combinations of retiagbine and sodium channel inhibitors for treating pains which are accompanied by an increase in muscle tone.

A number of different painful diseases are accompanied by an increase in skeletal muscle tone. In some cases, the pain generation is elicited by joint inflammations, and a painful body posture, which is frequently accompanied by painful muscle spasms, develops as a consequence. The treatment of these diseases includes benzodiazepines, for example; however, these compounds possess a marked potential for addiction and this limits their use. Frequently, treating the basic disease, e.g. the rheumatoid inflammation, does not result in corresponding, satisfactory therapeutic successes. For this reason, the additional administration of analgesics and/or skeletal muscle relaxants is often indicated.

In clinical practice, centrally acting muscle relaxants are used for alleviating abnormally elevated muscle tone in patients who are suffering from painful muscle spasms and/or rigidity in association with rheumatoid diseases or spasms in connection with neurological diseases. While a number of appropriate active compounds are available on the market, their clinical efficacy is frequently questionable or else limited by undesirable side effects.

The $Na^+$ channel-inhibiting substances constitute one class of these active compounds. Evidence exists that these substances are able to relieve an increase in muscle tone. It has been shown that, in clinically relevant concentration, propofol has a marked inhibitory effect on the sarcolemma sodium channels. This mechanism could contribute to reducing muscle tone (Haeseler et al., Anesth Analg 2001; 92:1192-8). It has also been shown that inhibiting the $Na^+$ channels inhibits neurotransmitter release from the presynaptic termini (Obrenovitch, Int Rev Neurobiol 1997; 40:109-35). The neuroprotective active compound riluzole is a sodium channel inhibitor and an antiexcitotoxic substance which is used for treating amyotrophic lateral sclerosis. Kennel et al. (J Neurol Sci 2000; 180:55-61) have recently shown that riluzole significantly delays the onset of the paralysis, and retards the progress of the functional parameters connected to muscle strength, in a mouse model of motoneuron disease. In a mouse model of heritable myotonia (De Luca et al., J Pharmacol Exp Ther 1997; 282:93-100), metilexin, an antiarrhythmic and antimyotonic substance, blocks the skeletal muscle sodium channels (Duranti et al., Eur J Med Chem 2000; 35:147-56) and relieves the hyperexcitability of the skeletal muscles. That the function of the skeletal muscle sodium channels is important in maintaining normal tone is supported by the fact that it has been possible to connect mutations in the gene for the α-subunit of the voltage-induced $Na^+$ channel (SCN4A) with inherited, nondystrophic myotonia. Interestingly, the myotonia resolved dramatically on administration of the $Na^+$ channel-inhibiting substance flecainide (Rosenfeld et al., Ann Neurol 1997; 42:811-4).

Tolperisone is a centrally acting muscle relaxant which is relatively well tolerated clinically. To date, relatively few publications have dealt with the mechanism of action of tolperisone-like compounds. Tolperisone suppresses transmission of the spinal segment reflex and effectively reduces C fiber-induced transmission in the afferent nerves both in vivo and in vitro (Farkas et al., Neurobiology 1997; 5:57-58). As compared with lidocaine, a local anesthetic, the substance has less of a blocking effect on transmission in the A fibers. It characteristic effect is that of strongly inhibiting the monosynaptic and polysynaptic spinal reflexes (Farkas et al. Neurobiology 1997; 5:57-58, Kocsis et al., Acta Pharm Hung 2002; 72(1):49-61, Okada et al., Jpn J Pharmacol 2001; 86:134-136). In rats, Ono et al. (J Pharmacobio Dynam 1984; 7:171-178) showed that tolperisone exhibits an effect like that of a local anesthetic ("membrane-stabilizing") both in motor neurons and in primary afferents in vivo as well as on the peripheral nerves in vitro. The effect of tolperisone appears to be similar to that of lidocaine, which is known to act as an inhibitor of voltage-dependent sodium channels (Strathmann 2002, www.ifap-index.de/bda/hausarzt/19-2002/6483.pdf). It has been shown that tolperisone, like lidocaine, blocks the tetrodotoxin (TTX)-sensitive and TTX-resistant currents and in this way gives rise to an inhibitory effect on both types of voltage-dependent sodium channels (Bastigkeit, MMW-Forschr Med 2000; 142:50-51, Farkas et al., 2000, http://www.asso.univparis5.fr/ewcbr/Francais/EWCBR2000/Abstracts/ABST126.htm; Kocsis et al., Acta Pharm Hung 2002; 72(1):49-61). It is probable that the mechanism of action of tolperisone in this connection differs somewhat from that of lidocaine. In addition, evidence exists that tolperisone lowers sodium permeability. This effect could be responsible for the excitability-reducing effect of tolperisone and consequently for the antispastic effect which has been recorded in clinical observations (Hinck and Koppenhofer, Gen Physiol Biophys 2001; 20:413-29). In addition, voltage-clamp experiments performed on snail neurons showed that tolperisone and its analogs inhibit voltage-dependent calcium flows (Novalies-Li et al., Eur J Pharmacol 1989; 168:299-305). Tolperisone analogs such as eperisone and silperisone exhibited similar behavior in electrophysiological experiments. Thus, it has been shown, for example, that silperisone reduces sodium permeability (During and Koppenhofer, Gen Physiol Biophys 2001; 20:157-73). It can be concluded from this that these substances might be able to reduce spastic skeletal muscle tone.

It has furthermore been shown, in clinical studies, that these substances are able to alleviate painful spasms which are associated with neurological or rheumatoid diseases. The effective employment of tolperisone in treating muscle spasms has been reported (Pratzel et al., Pain 1996; 67:417-25). Some derivatives of tolperisone, e.g. eperisone, also exhibited efficacy in the treatment of painful muscle spasms (Bose, Methods Find Exp Clin Pharmacol 1999; 21:209-13). Under certain pathological conditions, neurons are in a state of continuous depolarization, resulting in their sodium channels reacting more sensitively to the inhibitory effects of particular substances. This provides the possibility of alleviating muscle spasms and pain while preserving a favorable side-effect profile. More recent data indicate that tolperisone and its analogs exert selectively inhibitory effects on voltage-dependent sodium channels. This mechanism could be responsible for their spinal reflex-suppressing and muscle-relaxing effect. In addition, this property could produce the pain-alleviating effect which, because of the small differences which have been observed, could, in contrast to lidocaine, be free of side effects.

The potassium channel openers constitute another class of muscle-relaxing substances.

The substances include retigabine, for example. In in vitro analyses, it was shown that retigabine exerts multiple effects on sites which are connected with neurotransmission and membrane excitability. The primary mechanism of action appears to be based on a potassium channel opening which leads to marked stabilization of slightly depolarized, i.e.

hyperexcitable cells and can result in an elevated skeletal muscle tone being reduced (Rundfeldt and Netzer, Neurosci Letters 2000, 282:73-6).

Flupirtine is another representative of this substance class, which belongs to a class of triaminopyridines and which is used as a nonopioid analgesic possessing muscle-relaxing properties. It has been shown that flupirtine reduces skeletal muscle tone when it is used in doses which are comparable to those of the antinociceptive effect (Nickel et al., Arzn Forsch/Drug Res 1990a; 40:909-11).

More recent investigations demonstrate that flupirtine activates voltage-independent potassium channels (Kornhuber et al., J Neural Transm 1999; 106:857-67). This potassium channel-opening effect of flupirtine could be responsible for its analgesic and skeletal muscle-relaxing effect.

The prior art which has been described shows clearly that, while there are a number of substances which are used for treating pain conditions involving an increase in muscle tone, undesirable side effects frequently set limitations to their use. For example, at higher doses, flupirtine exhibits neurotoxic effects such as drowsiness and coordination disturbance. While tolperisone does not exhibit any severe undesirable side effects, its activity and the duration of its effect in connection with muscle relaxation are not satisfactory, possibly due to its relatively low bioavailability and its short half-life in humans (Ito et al., Arch Int Pharmacodyn Ther 1985; 275: 105-22), Matsunaga et al., Jpn J Pharmacol 1997; 73:215-20).

The object of this invention is therefore that of providing a pharmaceutical for treating pains which are accompanied by an increase in muscle tone, which pharmaceutical exhibits less serious side effects while having a comparable efficacy or else exhibits a higher activity at the same dose.

According to the invention, it is possible to achieve this by means of the novel combination of retigabine and a sodium channel inhibitor.

It was possible to show that the combination of sodium channel-inhibiting or -influencing active compounds and potassium channel openers increases the muscle-relaxing effect.

The following may, for example, be employed as $Na^+$ channel-inhibiting or -influencing substances: tolperisone and its analogs eperisone and silperisone, riluzole, propafenone, lidocaine, flecainide and metixen, as well as their pharmaceutically utilizable salts.

Particular preference is given, in this connection, to the combination of tolperisone, or its analogs, and retigabine, or their pharmaceutically utilizable salts. The combination according to the invention makes the treatment of pains which are accompanied by an increase in muscle tone more effective and more reliable. The combination of Na-channel inhibiting or -influencing substances and retigabine leads either to an increase in the therapeutic effect or an improvement in tolerability.

For example, it may be shown that Na channel-inhibiting or -influencing active compounds such as tolperisone can amplify the muscle-relaxing effect of retigabine, and vice versa. However, what is surprising, and unexpected for the skilled person, is, in particular, the effect that tolperisone superadditively amplifies the skeletal muscle-relaxing effect of retigabine and vice versa. By contrast, tolperisone does not amplify the side effects of retigabine.

The combination of the two substances can be used for treating pains in connection with diseases of the skeletal musculature which are accompanied by hypermyotonia and restricted mobility, in particular those which are elicited by injuries to the spinal cord, osteoporosis, arthritis and ankylosis/spastic conditions. It is also effective in connection with pains of the following origin: lumboischial pains, neurolathyrism, arthritis, diseases of the peripheral circulatory system, climacteric muscular and vascular complaints, trismus, myogenic headaches, rheumatic diseases which are accompanied by muscle hypertonia, spasms, pain, inflammatory symptoms and restricted mobility, and multiple sclerosis, and in the postoperative treatment of traumatic patients and for treating lower spastic paraparesis syndrome: lower paraspasm, transverse myelitis, multiple sclerosis, heritable inferior spastic paraplegia (Stuempel paraplegia), disturbances of the spinal blood circulation, cerebral paralysis involving lower spastic paresis, tetraparesis in connection with cervical myelopathy, vertebral dysplasia, tension headache and cervical brachialgia.

The combinations of $Na^+$ channel-inhibiting or -influencing active compounds and retigabine, and of their pharmaceutically utilizable salts, can be administered in all oral, enteral, rectal, lingual, intravenous, intramuscular, intraperitoneal, transdermal, subcutaneous or intracutaneous administration forms. Examples of preferred oral administration forms are tablets, film-coated tablets, sugar-coated tablets, hard gelatin capsules, soft gelatin capsules, chewing tablets, sucking tablets, syrup, controlled release preparations (for example dual formulation, delayed-release formulation), pellets, chewing tablets or soluble granules. Examples of other suitable administration forms are: solutions for injection, suspensions, suppositories, creams, ointments, gels, transdermal administration forms and subcutaneous or intracutaneous implants.

The substances can be administered simultaneously, consecutively or in a fixed combination. They can be administered together in one administration form or in two administration forms which can be identical or different. They can be administered simultaneously or consecutively, either briefly one after the other or at longer time intervals, for example retigabine in the evening and tolperisone in the morning.

The active compounds can be administered between 1 and 8 times daily, in an adequate quantity to achieve the desired affect. The active compounds are preferably administered from once to four times daily.

The daily dose should correspond to the approved quantities of the substances which are in each case employed in the combination.

The invention claimed is:

1. A method of treating neuralgia pain or neuropathic pain in a mammal comprising administering to said mammal a therapeutically effective amount of a combination of retigabine or a therapeutically utilizable salt thereof with a voltage-gated sodium channel inhibitor or a therapeutically utilizable salt thereof selected from the group consisting of tolperisone, eperisone, and silperisone.

2. The method of claim 1, where said pains are associated with neuralgias.

3. The method of claim 1, where said pains are associated with arthritis and arthrosis.

4. The method of claim 1, where said pains are associated with chronic or episodic tension headache.

5. The method of claim 1, where said pains originate from a cause selected from the group consisting of lower spastic paraparesis syndrome, disturbances of the spinal blood circulation, and cerebral paralysis involving lower spastic paresis.

6. The method of claim 1, where said pains originate from a cause selected from the group consisting of lower paraspasm, transverse myelitis, multiple sclerosis, heritable inferior spastic paraplegia, and Stuempel paraplegia.

7. The method of claim 1, where said pains are associated with tetraparesis in connection with cervical myelopathy, cervical brachialgia or vertebral dysplasia.

8. The method of claim 1, wherein said voltage-gated sodium channel inhibitor or therapeutically utilizable salt thereof is administered simultaneously with retigabine.

9. The method of claim 1, wherein retigabine, or a therapeutically utilizable salt thereof, and said voltage-gated sodium channel inhibitor are administered separately or consecutively.

10. The method of claim 1, wherein said neuralgia pain or neuropathic pain is accompanied by an increase in muscle tone.

11. The method of claim 1, wherein said mammal is a human.

* * * * *